(12) United States Patent
Cohen et al.

(10) Patent No.: US 9,050,293 B2
(45) Date of Patent: *Jun. 9, 2015

(54) SMALL MOLECULE SOLUBILIZATION SYSTEM

(75) Inventors: David M. Cohen, Lauderdale By The Sea, FL (US); Eugene R. Cooper, Berwyn, PA (US)

(73) Assignee: Juventio, LLC, Chatham, NJ (US)

( * ) Notice: Subject to any disclaimer, the term of this patent is extended or adjusted under 35 U.S.C. 154(b) by 714 days.

This patent is subject to a terminal disclaimer.

(21) Appl. No.: 12/503,929

(22) Filed: Jul. 16, 2009

(65) Prior Publication Data

US 2010/0016442 A1    Jan. 21, 2010

Related U.S. Application Data

(60) Provisional application No. 61/135,103, filed on Jul. 16, 2008.

(51) Int. Cl.
| | | |
|---|---|---|
| *A61K 31/164* | (2006.01) | |
| *A61K 9/00* | (2006.01) | |
| *A61K 47/10* | (2006.01) | |
| *A61K 47/24* | (2006.01) | |
| *A61K 47/38* | (2006.01) | |

(52) U.S. Cl.
CPC ............. *A61K 31/164* (2013.01); *A61K 9/0014* (2013.01); *A61K 47/10* (2013.01); *A61K 47/24* (2013.01); *A61K 47/38* (2013.01)

(58) Field of Classification Search
CPC ................................................... A61K 31/164
See application file for complete search history.

(56) References Cited

U.S. PATENT DOCUMENTS

| | | | |
|---|---|---|---|
| 4,091,090 A | | 5/1978 | Sipos |
| 4,552,872 A | | 11/1985 | Cooper et al. |
| 4,764,381 A | | 8/1988 | Bodor et al. |
| 4,885,174 A | | 12/1989 | Bodor et al. |
| 4,954,487 A | | 9/1990 | Cooper et al. |
| 4,983,396 A | | 1/1991 | Bodor et al. |
| 5,073,372 A | * | 12/1991 | Turner et al. .............. 424/401 |
| 5,196,410 A | | 3/1993 | Francoeur et al. |
| 5,534,242 A | | 7/1996 | Henry et al. |
| 5,534,246 A | | 7/1996 | Herb et al. |
| 5,585,398 A | | 12/1996 | Ernst |
| 5,853,732 A | | 12/1998 | Munden |

(Continued)

FOREIGN PATENT DOCUMENTS

| | | |
|---|---|---|
| CA | 2446060 A1 | 11/2002 |
| EP | 95813 A2 | 12/1983 |

(Continued)

OTHER PUBLICATIONS

United States District Court Southern District of Florida, Case No. 09-cv-60284-GRAHAM/TORRES, Complaint dated Feb. 20, 2009.

(Continued)

*Primary Examiner* — Paul Zarek
(74) *Attorney, Agent, or Firm* — Hoffmann & Baron, LLP

(57) ABSTRACT

The invention provides a drug delivery system for the topical administration of therapeutic agents, including therapeutic agent in an amount between 0.001 and 20% by weight, propylene glycol in an amount between 2 and 6% by weight, oleyl alcohol in an amount between 2 and 6% by weight, and a volatile component in an amount between 60 and 95% by weight.

15 Claims, 1 Drawing Sheet

(56) References Cited

U.S. PATENT DOCUMENTS

| | | | |
|---|---|---|---|
| 5,891,462 | A | 4/1999 | Carrara et al. |
| 6,295,469 | B1 | 9/2001 | Linkwitz et al. |
| 6,319,913 | B1 | 11/2001 | Mak et al. |
| 6,528,086 | B2 | 3/2003 | Zhang |
| 6,579,865 | B2 | 6/2003 | Mak et al. |
| 6,635,674 | B1 | 10/2003 | Kaneko et al. |
| 6,894,078 | B2 | 5/2005 | Castillo |
| 7,157,097 | B2 | 1/2007 | Mak et al. |
| 7,273,887 | B1 | 9/2007 | Wepfer |
| 7,335,379 | B2 | 2/2008 | Carrara et al. |
| 7,504,114 | B1 | 3/2009 | Kurita et al. |
| 2003/0027833 | A1 | 2/2003 | Cleary et al. |
| 2003/0054017 | A1 | 3/2003 | Castillo |
| 2004/0131665 | A1 | 7/2004 | Wepfer |
| 2004/0162989 | A1 | 8/2004 | Kirovski |
| 2004/0175416 | A1 | 9/2004 | Taravella et al. |
| 2004/0208914 | A1* | 10/2004 | Richlin et al. ............... 424/448 |
| 2005/0014823 | A1 | 1/2005 | Soderlund et al. |
| 2005/0276842 | A1 | 12/2005 | Zhang et al. |
| 2005/0281750 | A1 | 12/2005 | Willcox et al. |
| 2006/0155922 | A1 | 7/2006 | Gorobets et al. |
| 2006/0280783 | A1 | 12/2006 | Dipietro et al. |
| 2007/0015590 | A1 | 1/2007 | Jackson et al. |
| 2007/0189978 | A1 | 8/2007 | Zhang et al. |
| 2007/0269393 | A1 | 11/2007 | Wepfer |
| 2008/0176948 | A1 | 7/2008 | Cohen et al. |
| 2009/0048347 | A1 | 2/2009 | Cohen et al. |
| 2010/0016442 | A1 | 1/2010 | Cohen et al. |

FOREIGN PATENT DOCUMENTS

| | | |
|---|---|---|
| EP | 129283 | 12/1984 |
| EP | 302147 A1 | 2/1989 |
| EP | 1293203 A1 | 3/2003 |
| WO | 9529678 A1 | 11/1995 |
| WO | 02096435 A2 | 12/2002 |
| WO | 2004030665 A1 | 4/2004 |
| WO | 2005097196 A2 | 10/2005 |
| WO | 2007031753 A2 | 3/2007 |
| WO | 2007038325 A2 | 4/2007 |
| WO | 2007070643 A2 | 6/2007 |
| WO | 2007070679 A2 | 6/2007 |
| WO | 2007070694 A2 | 6/2007 |
| WO | 2007070695 A2 | 6/2007 |
| WO | WO 2007070679 A2 * | 6/2007 |
| WO | 2008005240 A2 | 1/2008 |
| WO | 2009026178 A2 | 2/2009 |

OTHER PUBLICATIONS

United States District Court Southern District of Florida, Case No. 09-cv-60284-GRAHAM/TORRES, Defendant's Answer to Plaintiff's Complaint with Affirmative Defenses and Counterclaim dated Mar. 23, 2009.

International Search Report for PCT/US2009/004173 dated Jun. 26, 2008.

United States District Court Southern District of Florida, Case No 09-cv-60284-GRAHAM/TORRES, Condensed Transcript of Confidential Deposition dated Mar. 11, 2009.

United States District Court Southern District of Florida, Case No. 09-cv-6084-GRAHAM/TORRES, Settlement Agreement and Release dated Sep. 11, 2009.

Galinsky et al., "Basic Pharmacokinetics and Pharmacodynamics," Remington: The Science and Practice of Pharmacy, (2006) p. 1171, Lippincott Williams & Wilkins, Baltimore.

Rodu et al., "Clinical and chemical properties of a novel mucosal bioadhesive agent," J Oral Pathol., (1988) 17:9-10.

Cooper, E., "Vehicle Effects on Skin Penetration," Percutaneous Absorption, (1985) pp. 525-529, R .L. Bronaugh and H. I. Maibach,Eds., Marcel Dekker, Inc. New York.

Cooper, E. R., "Increased Skin Permeability for Lipophilic Molecules," J. Pharm. Sci. (1984) pp. 1153-1156 73:8.

Cooper, E. R, et al., "Effect of Fatty Acids and Alcohols on the Penetration of Acyclovir Across Human Skin in Vitro," J. Pharm., Sci., (1985) pp. 688-689, 74:6.

Cooper, E. R. et al., "Skin Permeability," Methods in Skin Research, (1985) pp. 407-432, D. Skerrow and C. J. Skerrow, Eds., John Wiley and Sons, Chichester.

Material Safety Data Sheet Cyclohexylmethanol, 99%. Fisher Scientific [online], Mar. 7, 2006 [retrieved on Apr. 20, 2008] Retrieved from the Internet USR:<https://fscimage.fishersci.com/msds/46753.htm>.

Merritt, E. W. et al., "Diffusion Apparatus for Skin Penetration," J. Controlled Release (1984) 1:161-162.

Vaida, et al., "Prolongation of lidocaine spinal anesthesia with phenylephrine," Anesthesia and Analgesia, (1986) pp, 781-785, 65:7.

Williams, et al., "Benzyl alcohol Attenuates the Pain of Lidocaine Injections and Prolongs anesthesia," J. Dermatol Surg Oncol, (1994) 20:730-733.

Kondo, S. at al., "Enhancement of Transdermal Delivery by Superfluous Thermodynamic Potential, III. Percutaneous Absorption of Nifedipien in Rats," J. Pharmacobic-Dyn., (1987), pp. 743-794, vol. 10.

International Search Report for PCT/US08/051176 dated May 20, 2008.

International Search Report for PCT/US2009/004172 dated Dec. 7, 2009.

International Preliminary Report of Patentability and Written Opinion for PCT/US2008/051176 dated Jul. 21, 2009.

International Preliminary Report of Patentability for PCT/US08/04173 dated Jul. 27, 2009.

Cooper, E. et al., "Transport Across Epithelial Members," J. Controlled Release (1987) 6:23.

* cited by examiner

SMALL MOLECULE SOLUBILIZATION SYSTEM

RELATED APPLICATIONS

This application claims the benefit of priority to U.S. Provisional Patent Application No. 61/135,103, filed Jul. 16, 2008, which application is hereby incorporated by reference in its entirety.

BACKGROUND

The medical community is continually engaged in efforts to enhance the effective delivery of drugs across the skin. Many of the concerns associated with oral administration can often be avoided by topically administering an active agent to a subject in need thereof. For example, reliable delivery of a pharmaceutically active agent to organs or tissues in need thereof via oral administration is often difficult due to variable rates of absorption and metabolism associated with oral delivery. In contrast, topical administration of a pharmaceutically active agent can provide high doses of the active agent directly to the desired area, often minimizing side effects.

One such way of delivering drugs across the skin surface is by way of a non-occlusive transdermal and/or topical dosage form. Some non-limiting examples of non-occlusive transdermal and topical semi-solid dosage forms include creams, ointments, gels, foams, sprays, solutions, and lotions (i.e., emulsions, or suspensions). However, the inefficiencies of drug permeation across the skin are well known. In fact, the permeation of a drug in a non-occlusive transdermal dosage form can be as little as 1% and usually is no more than 15%. Thus, a vast majority of the active drug remains unabsorbed on the skin. Because the vast majority of the drug does not penetrate the skin surface, the bioavailability of the particular drug is not optimal, and a high risk of contamination of other individuals in close proximity to the user is presented by the unwanted transfer of the pharmaceutical formulation in the non-occlusive dosage form. Various methods have been tried to improve the percutaneous absorption of pharmacologically active substances. For example, pharmacologically active substances were modified to form prodrugs and complexes. However, administration of these agents requires detailed studies on the individual pharmacologically active substance, resulting in large monetary and time investments.

Occlusive dosage forms present some advantages over non-occlusive dosage forms, such as assisting the rate of penetration of drugs across the skin. However, occlusive dosage forms also exhibit several major drawbacks. For example, occlusive dosage forms present a high potential of local irritation caused by the prolonged contact of the drug, volatiles, vehicle excipients, and the adhesive used to attach the occlusive device, e.g., the patch, to the skin. In addition, the occlusive nature of certain dosage forms, such as the patch device, also restrict the natural ability of the skin to "breathe," thereby increasing the risk of irritation. In addition to the aforementioned drawbacks of occlusive dosage forms, significant serious hazards have been documented regarding the high drug loading that is specific to patches.

Although attempts have been made to overcome drawbacks associated with both occlusive and non-occlusive topical drug forms, such attempts have been unsuccessful. Accordingly, there remains a need to provide a pharmaceutically acceptable topical pharmaceutical formulation system that overcomes the disadvantages of these systems.

SUMMARY OF INVENTION

The present invention provides a drug delivery system for topical administration of a therapeutic agent comprising a therapeutic agent, an alkane diol, a $C_8$-$C_{34}$ fatty acid or corresponding alcohol or ester having a melting point below 40° C., and a volatile component. In certain embodiments, the therapeutic agent is present in an amount such that upon topical application to a surface, evaporation of the volatile component occurs such that the remaining solution is near saturation, at saturation, or above saturation with the therapeutic agent at the temperature of the surface.

For example, the present invention provides a drug delivery system for topical administration of a therapeutic agent comprising i) a first component which is a therapeutic agent, such as any one of the therapeutic agents listed below, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature, or any $C_{12}$ to $C_{22}$ mono- or poly-unsaturated or branched chain alcohol or corresponding acid which is a liquid at room temperature, and iv) a fourth component which is a volatile component, such as one or more short-chain alcohols, volatile silicones, or combinations thereof.

In certain embodiments, the drug delivery system of the present invention may further comprise a thickener, such as any suitable thickener that is soluble in the total solvent system.

The present invention also provides a method for administering the drug delivery system of the present invention to an animal in need of such treatment comprising applying an effective amount of the drug delivery system according to the present invention.

The present invention further provides a method for the treatment or prophylaxis of a disease or condition in an animal which comprises administering to a dermal surface of an animal in need of such treatment a therapeutically effective amount of a drug delivery system according to the present invention.

DETAILED DESCRIPTION OF THE DRAWINGS

FIG. 1 shows the six zones of the lateral periocular regions for administration of dermatological injections.

DETAILED DESCRIPTION OF THE INVENTION

The present invention provides a drug delivery system for topical administration of a therapeutic agent comprising a therapeutic agent, an alkane diol, a $C_8$-$C_{34}$ fatty acid or corresponding alcohol or ester having a melting point below 40° C., and a volatile component. In certain embodiments, the therapeutic agent is present in an amount such that upon topical application to a surface, evaporation of the volatile component occurs such that the remaining solution is near saturation, at saturation, or above saturation with the therapeutic agent at the temperature of the surface.

In certain embodiments, the drug delivery system comprises between 0.001 and 20 percent by weight of the therapeutic agent (e.g., any one of the therapeutic agents listed below), such as between 0.01 and 20 percent, or 0.1 and 20 percent by weight of the therapeutic agent. In certain embodiments, the drug delivery system comprises between four and eight percent by weight of the therapeutic agent (e.g., any one of the therapeutic agents listed below).

In certain embodiments, the alkane diol comprises a C3 or C4 alkane diol. In certain such embodiments, the alkane diol is selected from propylene glycol or a butane diol with adjacent hydroxyl groups, such as butane-1,2-diol or butane-2,3-diol. In certain embodiments, the drug delivery system comprises between two and 35 percent by weight of the alkane diol, such as between two and 30 percent by weight of the alkane diol. In certain embodiments, the drug delivery system comprises between two and eight percent by weight of the alkane diol. In certain such embodiments, the drug delivery system comprises between two and six percent by weight of the alkane diol, such as between three and five percent by weight of the alkane diol, such as four percent by weight of the alkane diol. In certain embodiments, the alkane diol comprises propylene glycol, an organic compound known also by the systematic name propane-1,2-diol.

In certain embodiments, the $C_8$-$C_{34}$ fatty acid or corresponding alcohol or ester having a melting point below 40° C. comprises a $C_8$-$C_{24}$ fatty acid or corresponding alcohol or ester having a melting point below 40° C. In certain embodiments, the $C_8$-$C_{34}$ fatty acid or corresponding alcohol or ester is liquid at room temperature (e.g., is liquid at 21-24° C.). In certain embodiments, the ester is a methyl ester. In certain embodiments the $C_8$-$C_{34}$ fatty acid or corresponding alcohol or ester having a melting point below 40° C. is selected from oleyl alcohol, oleic acid, ester derivatives of oleic acid such as the methyl ester, any $C_{10}$ to $C_{14}$ saturated alcohol or corresponding acid or ester which is a liquid at room temperature (e.g., is liquid at 21-24° C.), or any $C_{12}$ to $C_{22}$ mono- or poly-unsaturated or branched chain alcohol or corresponding acid or ester which is a liquid at room temperature (e.g., is liquid at 21-24° C.). In certain embodiments, the $C_8$-$C_{34}$ fatty acid or corresponding alcohol or ester having a melting point below 40° C. is selected from a $C_{10}$ to $C_{14}$ saturated alcohol, $C_{12}$ mono- or polyunsaturated alcohol or branched-chain alcohol that is a liquid-at-room-temperature (e.g., is liquid at 21-24° C.), a $C_{10}$ to $C_{14}$ saturated acid, and a $C_{12}$ mono- or polyunsaturated acid or branched-chain acid that is a liquid-at-room-temperature (e.g., is liquid at 21-24° C.). In certain embodiments, the drug delivery system comprises between two and 30 percent by weight of the $C_8$-$C_{34}$ fatty acid or corresponding alcohol or ester having a melting point below 40° C. In certain embodiments, the drug delivery system comprises between two and seven percent by weight of the $C_8$-$C_{34}$ fatty acid or corresponding alcohol or ester having a melting point below 40° C. In certain such embodiments, the drug delivery system comprises between two and six percent by weight of the $C_8$-$C_{34}$ fatty acid or corresponding alcohol or ester having a melting point below 40° C., such as between three and five percent by weight of the $C_8$-$C_{34}$ fatty acid or corresponding alcohol or ester having a melting point below 40° C., such as four percent by weight of the $C_8$-$C_{34}$ fatty acid or corresponding alcohol or ester having a melting point below 40° C. In certain embodiments, the $C_8$-$C_{34}$ fatty acid or corresponding alcohol or ester having a melting point below 40° C. comprises oleic acid or oleyl alcohol.

Generally, the fatty alcohol can be a $C_{10}$ to $C_{14}$ saturated alcohol, a $C_{12}$ to $C_{22}$ mono- or polyunsaturated alcohol or branched-chain alcohol that is a liquid at room temperature, or those same compounds in acid form. Fatty alcohols are aliphatic alcohols derived from natural fats and oils. They are the counterparts of fatty acids. They usually (but not always) have an even number of carbon atoms. They find use in the cosmetics and food industry. Fatty alcohols are a common component of waxes, mostly as esters with fatty acids but also as alcohols themselves. Those with common names include capryl alcohol (1-octanol; 8 carbon atoms); pelargonic alcohol (1-nonanol; 9 carbon atoms); capric alcohol (1-decanol; 10 carbon atoms); lauryl alcohol (1-dodecanol; 12 carbon atoms); myristyl alcohol (1-tetradecanol; 14 carbon atoms); palmitoleyl alcohol (cis-9-hexadecan-1-ol; 16 carbon atoms, unsaturated, $CH_3(CH_2)_5CH=CH(CH_2)_8OH$); isostearyl alcohol (16-methylheptadecan-1-ol; 18 carbon atoms, branched, $(CH_3)_2CH-(CH_2)_{15}OH$); elaidyl alcohol (9E-octadecen-1-ol; 18 carbon atoms, unsaturated, $CH_3(CH_2)_7CH=CH(CH_2)_8OH$); oleyl alcohol (cis-9-octadecen-1-ol; 18 carbon atoms, unsaturated); linoleyl alcohol (9Z,12Z-octadecadien-1-ol; 18 carbon atoms, polyunsaturated); elaidolinoleyl alcohol (9E,12E-octadecadien-1-ol; 18 carbon atoms, polyunsaturated); linolenyl alcohol (9Z,12Z, 15Z-octadecatrien-1-ol; 18 carbon atoms, polyunsaturated); elaidolinolenyl alcohol (9E,12E, 15-E-octadecatrien-1-ol; 18 carbon atoms, polyunsaturated); ricinoleyl alcohol (12-hydroxy-9-octadecen-1-ol; 18 carbon atoms, unsaturated, diol, $CH_3(CH_2)_5CH(OH)CH_2CH=CH(CH_2)_8OH$); arachidyl alcohol (1-eicosanol; 20 carbon atoms); behenyl alcohol (1-docosanol; 22 carbon atoms); erucyl alcohol (cis-13-docosen-1-ol; 22 carbon atoms, unsaturated, $CH_3(CH_2)_7CH=CH(CH_2)_{12}OH$); lignoceryl alcohol (1-tetracosanol; 24 carbon atoms); ceryl alcohol (1-hexacosanol; 26 carbon atoms); montanyl alcohol (1-octacosanol; 28 carbon atoms); myricyl alcohol (1-triacontanol; 30 carbon atoms); and geddyl alcohol (1-tetratriacontanol; 34 carbon atoms).

In certain embodiments, the volatile component comprises one or more short-chain alcohols, volatile silicones, or combinations thereof. In certain embodiments, the volatile component comprises a non-aqueous volatile solvent. In certain embodiments, the short-chain alcohol is selected from the isomers of butanol, isomers of propanol, ethanol, and methanol. Alternatively, any other short-chain alcohol safe for topical administration would be appropriate. In certain embodiments, the volatile component comprises a short-chain alcohol other than methanol. In certain such embodiments, the volatile component comprises ethanol, propanol, isopropanol, butanol, or butan-2-ol. In certain embodiments, the volatile component comprises ethanol or isopropanol. In certain embodiments, the volatile component comprises a combination of one or more volatile solvents, such as a combination of one or more short-chain alcohols. In certain such embodiments, the volatile component comprises a combination of one or more volatile solvents selected from ethanol, propanol, isopropanol, butanol, and butan-2-ol. In certain embodiments, the volatile component comprises one or more volatile silicones. In certain embodiments, the volatile silicone is odorless and/or has a low heat of evaporation so it does not create a cold sensation when evaporating after being deposited on the skin. In certain embodiments, the volatile silicone comprises a volatile polydimethylsiloxane. Exemplary volatile silicone compounds include, but are not limited to, volatile, low molecular weight polydimethylsiloxane compounds. Such compounds can be either a linear or a cyclic polydimethylsiloxane compound having a viscosity from about 0.5 to about 10 cst (centistokes). In certain embodiments, the volatile silicone comprises the cyclic, volatile, low molecular weight polydimethylsiloxanes designated as cyclomethicones. Suitable cyclomethicones are available commercially under the trade names DOW CORNING 244 Fluid, DOW CORNING 245 Fluid, DOW CORNING 344 Fluid and DOW CORNING 345 Fluid from DOW CORNING Corporation, Midland, Mich., and SILICONE SF-1173 and SILICONE SF-1202 from General Electric, Waterford, N.Y. In certain embodiments, the volatile silicone comprises a linear, low molecular weight, volatile polydimethylsiloxane compound designated as hexamethyldisiloxane, decamethyltetrasiloxane, octamethyltrisiloxane, or decamethylpentasiloxane. In certain embodiments, the volatile silicone comprises hexamethyldisiloxane having a viscosity of 0.65 cST.

In certain embodiments, the volatile component comprises a combination of a volatile silicone and one or more short-chain alcohol. In certain embodiments, the drug delivery system comprises between 60 and 90 percent by weight of the volatile component, such as between 60 and 85 percent by weight of the volatile component.

For example, the present invention provides a drug delivery system for topical administration of a therapeutic agent comprising i) a first component which is a therapeutic agent, such as any one of the therapeutic agents listed below, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature (e.g., is liquid at 21-24° C.), or any $C_{12}$ to $C_{22}$ mono- or poly-unsaturated or branched chain alcohol or corresponding acid which is a liquid at room temperature (e.g., is liquid at 21-24° C.), and iv) a fourth component which is a volatile component, such as one or more short-chain alcohols, volatile silicones, or combinations thereof.

In certain embodiments, the drug delivery system of the present invention may further comprise a thickener, such as any suitable thickener that is soluble in the total solvent system. In certain embodiments, the thickener is soluble in the volatile component of the drug delivery system. Examples of thickeners that may be used in the drug delivery system of the present invention include cellulose derivatives, such as polymers comprising carboxymethyl-, hydroxyethyl-, hydroxypropyl-, hydroxypropylmethyl- or methyl-cellulose; synthetic polymers, such as those comprising polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxyethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide, hyaluronic acid (e.g., hydrazine cross-linked hyaluronic acid), and silicone; natural gums, such as those comprising alginates, carrageenan, guar-gum, gelatine, tragacanth, (amidated) pectin, xanthan, chitosan collagen, agarose; mixtures and further derivatives or co-polymers thereof and/or other pharmaceutically acceptable polymers. In certain embodiments, the drug delivery system of the present invention further comprises hydroxypropylcellulose. Pharmaceutical-grade hydroxypropylcellulose is commercially available in a variety of molecular weights, any of which would be suitable in the formulation of the current invention. In certain embodiments of the present invention wherein the drug delivery system further comprises a thickener, the drug delivery system comprises between 0.1 and 3.5 percent by weight of the thickener. In certain such embodiments, the drug delivery system comprises between 2.5 and 3.5 percent by weight of the thickener.

In certain embodiments, the drug delivery system of the present invention comprises a thickener and a volatile silicone. In certain embodiments, the drug delivery system of the present invention comprises a thickener and a volatile silicone, wherein the thickener is hydroxypropylcellulose (HPC). In certain such embodiments, the drug delivery system comprises between about 2.5 and about 3.5 percent by weight of hydroxypropylcellulose (HPC).

The present invention also provides a method for administering the drug delivery system of the present invention to an animal in need of such treatment comprising applying an effective amount of the drug delivery system according to the present invention, e.g., to the skin of the animal.

The present invention further provides a method for the treatment or prophylaxis of a disease or condition in an animal which comprises administering to a dermal surface of an animal in need of such treatment a therapeutically effective amount of a drug delivery system according to the present invention.

In certain embodiments, the animal is a human.

Specific non-limiting examples of therapeutic agents that can be used in the pharmaceutical compositions of the present invention include analgesics and anti-inflammatory agents, anti-helminthics, anti-anginal agents (e.g., nitrates), anti-arrhythmic agents, anti-arthritics, anti-asthma agents, anti-bacterial agents, anti-viral agents, anti-coagulants, anti-depressants, anti-diabetics, anti-emetics, anti-epileptics, anti-fungal agents, anti-gout agents, anti-hypertensive agents, anti-malarials, anti-migraine agents, anti-muscarinic agents, anti-neoplastic agents and immunosuppressants, anti-parkinsonian agents, anti-psychotics, anti-protozoal agents, anti-spasmodics, anti-thrombotic agents, anti-thyroid agents, anti-tussives, anxiolytic, sedatives, hypnotics and neuroleptics, beta-blockers, cardiovascular drugs, cardiac inotropic agents, cerebral vasodilators, chemotherapeutic agents, cholinergic antagonists, contraceptives, coronary vasodilators, corticosteroids, diuretics, anti-parkinsonian agents, gastro-intestinal agents, histamine (e.g., $H_1$ and $H_3$) receptor antagonists, immunosuppressive agents, keratolytics, lipid regulating agents, muscle relaxants, narcotic antagonists, opioids, peripheral vasodilators, anti-anginal agents, nutritional agents, analgesics, sex hormones, stimulants, vitamins and anesthetics.

Examples of such therapeutic agents include without limitation: 3-ketodesogestrel, 4-dihydrotestosterone, abecarnil, acamprostate, acavir, acebutolol, aceclofenac, acemetacin, acetaminophen, acetaminosalol, acetanilide, acetohexamide, acetophenazine maleate, acetophenazine, acetoxolone, acetoxypregnenolone, acetretin, acrisorcin, acrivastine, acyclovir, adinazolam, adiphenine hydrochloride, adrafinil, adrenolone, agatroban, ahnitrine, akatinol, alatrofloxacin, albendazole, albuterol, aldioxa, alendronate, alfentanil, alibendol, alitretinoin, allopurinol, allylamines, allylestrenol, alminoprofen, almotriptan, alosetron, aloxiprin, alprazolam, alprenolol, amantadine, ambucetamide, amidephrine, amidinomycin, amiloride, aminoarylcarboxylic acid derivatives, aminoglutethimide, aminoglycosides, aminopentamide, aminopromazine, aminorex, amiodarone, amiphenazole, amiprilose, amisulpride, amitriptyline, amlexanox, amlodipine, amodiaquine, amosulalol, amotriphene, amoxapine, amoxicillin, amphecloral, amphetamine, amphomycin, ampicillin, ampiroxicam, amprenavir, amrinone, amsacrine, amyl nitrate, amylobarbitone, anagestone acetate, anastrozole, andinocillin, androstenediol, androstenediol-17-acetate, androstenediol-17-benzoate, androstenediol-3-acetate, androstenediol-3-acetate-17-benzoate, androstenedione, androsterone acetate, androsterone benzoate, androsterone propionate, androsterone, angiotensin, anidulafungin, aniracetam, apazone, apicycline, apoatropine, apomorphine, apraclonidine, aprepitant, aprotinin, arbaprostil, ardeparin, aripiprazole, arnikacin, arotinolol, arstiinol, arylacetic acid derivatives, arylalkylamines, arylbutyric acid derivatives, arylcarboxylic acids, arylpiperazines, arylpropionic acid derivatives, aspirin, astemizole, atenolol, atomoxetine, atorvastatin, atovaquone, atropine, auranofin, azapropazone, azathioprine, azelastine, azetazolamide, azithromycin, baclofen, bambuterol, bamethan, barbitone, barnidipine, basalazide, beclamide, beclobrate, beclomethasone, befimolol, bemegride, benazepril, bencyclane, bendazac, bendazol, bendroflumethiazide, benethamine penicillin, benexate hydrochloride, benfurodil hemisuccinate, benidipine, benorylate, bentazepam, benzhexol, benziodarone, benznidazole, benzoctamine, benzodiazepine derivatives, benzodiazepine, benzonatate, benzphetamine, benzylmorphine, beperiden, bephenium hydroxynaphthoate, bepridil, bepridil, betahistine, betamethasone, betaxolol, bevantolol, bevonium methyl sulfate, bexarotene, bezafibrate, bialamicol, biapenem, bicalutamide, bietamiverine, binedaline, binifibrate, biricodar, bisacodyl, bisantrene, bisoprolol, bitolterol, bopindolol, boswellic acid, bradykinin, bretylium, bromazepam, bromocriptine, bromperidol, brotizolam, brovincamine, buciclate, bucloxic acid, bucumolol, budesonide, budralazine, bufeniode, bufetolol, buflomedil, bufuralol, bumetanide, bunitrolol, bupranolol, buprenorphine, buprorion, buspirone, busulfan, butalamine, butarphenol, butaverine, butidrine hydrochloride, butobarbitone, butoconazole, butofilol, butorphenol, butropium bromide, cabergoline, calcifediol, calcipotriene, calcitriol, caldiribine, cambendazole, camioxirole, camostat, camptothecin, candesartan, candoxatril, capecitabine, caprate, capsaicin, captopril, carazolol, carbacephems, carbamates, carbamezepine, carbapenems, carbarsone, carbatrol, carbenoxolone, carbimazole, carbromal, carbuterol, carisoprodol, carotenes, caroverine, carteolol, carvedilol, cefaclor, cefazolin, cefbuperazone, cefepime, cefoselis, ceftibuten, celcoxib, celecoxib, celiprolol, cephaeline, cephalosporin C, cephalosporins, cephamycins, cerivastatin, certoparin, cetamolol, cetiedil, cetirizine, cetraxate, chloracizine, chlorambucil, chlorbetamide, chlordantoin, chlordiazepoxide, chlormadinone acetate, chlormethiazole, chloroquine, chlorothiazide, chlorpheniramine, chlorphenoxamide, chlorphentermine, chlorproguanil, chlorpromazine, chlorpropamide, chlorprothixene, chlortetracycline, chlorthalidone, cholecalciferol, chromonar, ciclesonide, ciclonicate, cidofivir, ciglitazone, cilansetron, cilostazol, cimetidine, cimetropium bromide, cinepazet maleate, cinnamedrine, cinnarizine, cinolazepam, cinoxacin, ciprofibrate, ciprofloxacin, cisapride, cisplatin, citalopram, citicoline, clarithromycin, clebopride, clemastine, clenbuterol, clidanac, clinofibrate, clobazam, clobenfurol, clobenzorex, clofazimine, clofibrate, clofibric acid, cloforex, clomipramine, clonazepam, clonidine, clonitrate, clopidogrel, clopirac indomethacin, cloranolol, cloricromen, clorprenaline, clortermine, clotiazepam, cloxacillin, clozapine, cinepazide, codeine methyl bromide, codeine phosphate, codeine sulfate, codeine, colloidal bismuth subcitrate, cortisone, cromafiban, cromolyn, cropropamide, crotethamide, curcumin, cyclandelate, cyclarbamate, cyclazocine, cyclexedrine, cyclizine, cyclobenzaprine, cyclodrine, cyclonium iodide, cyclopentamine, cyclosporine, cypionate, cyproheptadine, cyproterone acetate, cyproterone, cytarabine, dacarbazine, dalfopristine, dantrolene sodium, dapiprazole, darodipine, decanoate, decitabine, decoquinate, dehydroemetine, dehydroepiandrosterone, delavirdine, delaviridine, demeclocycline, denopamine, deramciclone, descitalopram, desipramine, desloratadine, desogestrel, desomorphine, desoxymethasone, detomidine, dexamethasone, dexamphetamine, dexanabinol, dexchlorpheniramine, dexfenfluramine, dexmethylphenidate, dexrazoxane, dextroamphetamine sulfate, dextroamphetamine, dextropropoxyphene, DHEA, diacetate, diamorphine, diazemine, diazepam, diazoxide, dibromopropamidine, dichlorophen, diclofenac, dicoumarol, didanosine, dideoxyadenosine, diethylpropion, difemerine, difenamizole, diflunisal, digitoxin, digoxin, dihydroergotamine, dihydrocodeine, dihydrocodeinone enol acetate, dihydroergotamine mesylate, dihydroergotamine, dihydrogesterone, dihydromorphine, dihydropyridine derivatives, dihydrostreptomycin, dihydrotachysterol, dihydroxyaluminum acetylsalicylate, diiodohydroxyquinoline, diisopromine, dilazep, dilevalol, diltiazem, diloxanide furoate, diloxanide, diltiazem, dimefline, dimenhydrinate, dimethisterone, dimetofrine, dimorpholamine, dinitolmide, dioxaphetyl butyrate, dioxethedrine, dipheniethoxidine, diphenhydramine, diphenoxylate, diphetarsone, dipivefrin, diponium bromide, dipyridamole, dirithromycin, disopyramide, divalproex sodium, dofetilide, domperidone, donezepil, dopexamine, dopradil, dosmalfate, doxapram, doxazosin, doxefazepam, doxepin, doxycycline, drofenine, dromostanolone propionate, dromostanolone, dronabinol, droperidol, droprenilamine, d-threomethylphenidate, duloxetine, dutasteride, ebrotidine, eburnamonine, ecabet, ecenofloxacine, edavarone, edoxudine, efavirenz, effivarenz, efloxate, eledoisin, eletriptan, elgodipine, ellipticine, emepronium bromide, emetine, enalapril, enanthate, encainide, enlopitat, enoximone, enprostil, entacapone, epanolol, ephedrine, epinastine, epinephrine, epirubicin, eplerenone, eposartan, ergocalciferol, ergoloid mesylates, ergotamine, ertapenem, erythromycin, erytlirityl tetranitrate, esaprazole, escitalopram, esmolol, esomeprazole, esonarimod, estazolam, estradiol benzoate, estradiol, estramustine, estriol succinate, estriol, estrone acetate, estrone sulfate, etafedrine, etafenone, ethacrynic acid, ethamivan, ethinamate, ethinylestradiol 3-acetate, ethinylestradiol 3-benzoate, ethinylestradiol, ethionamide, ethisterone (17α-ethinyltestosterone), ethopropazine, ethotoin, ethoxyphenamine, ethylestrenol, ethylmorphine, ethylnorepinephrine, ethynodiol diacetate, etodolac, etofibrate, etoposide, etoricoxib, etretinate, everolimus, exalamide, examestane, examorelin, ezemitibe, falecalcitriol, famciclovir, famotidine, fantofarone, farapenum, farglitazar, fasudil, felbamate, felodipine, fenalamide, fenbufen, fenbutrazate, fendiline, fenfluramine, fenofibrate, fenofibric acid, fenoldopam, fenoprofen, fenoterol, fenoverine, fenoxazoline, fenoxedil, fenpiprane, fenproporex, fenspiride, fentanyl, fexofenadine, flavoxate, flecainide, flopropione, floredil, floxuridine, fludarabine, fludiazepam, fludrocortisone, flufenamic acid, flunanisone, flunarizine, flunisolide, flunitrazepam, fluocortolone, fluoxetine, flupenthixol decanoate, fluphenazine decanoate, fluphenazine enanthate, fluphenazine, fluproquazone, flurazepam, flurbiprofen, flurogestone acetate, fluticasone propionate, fluvastatin, fluvoxamine, fominoben, formoterol, foscarnet, fosinopril, fosphenyloin, frovatirptan, fudosteine, fumagillin, furazolidone, furazolidone, furfurylmethyl amphetamine, furosemide, gabapentin, gabexate, gaboxadol, galanthamine, gallopamil, gammaparin, ganciclovir, ganglefene, gefarnate, gemcitabine, gemfibrozil, gepirone, gestadene, ghrelin, glatiramer, glaucarubin, glibenclamide, gliclazide, glimepiride, glipizide, gluconic acid, glutamicacid, glyburide, glyceryl trinitrate, glymepiride, granisetron, grepafloxacin, guaiazulene, guanabenz, guanfacine, halofantrine, haloperidol decanoate, haloperidol, haloxazolam, hepronicate, heptanoate, hexobendine, hexoprenaline, hydramitrazine, hydrazides, hydrochlorothiazide, hydrocodone, hydrocortisone, hydromorphone, hydroxyamphetamine, hydroxymethylprogesterone acetate, hydroxymethylprogesterone, hydroxyprogesterone acetate, hydroxyprogesterone caproate, hydroxyprogesterone, hymecromone, hyoscyamine, ibopamine, ibudilast, ibufenac, ibuprofen, ibutilide, idebenone, idoxuridine, ifenprodil, igmesine, iloprost, imatinib, imidapril, imidazoles, imipenem, imipramine, imolamine, incadronic acid pergolide, indanazoline, indenolol, indinavir, indomethacin, indoramin, inosinepranobex, inositol niacinate, iodoquinol, ipidracine, iproniazid, irbesartan, irinotecan, irsogladine, isobutyrate, isocaprate esters, isoetharine, isometheptene, isoproterenol, isosorbide dinitrate, isosorbide mononitrate, isosorbide dinitrate, isoxsuprine, isradipine, itasetron, itramintosylate, ivermectin, kallidin, kallikrein, kanamycin, ketamine, ketoprofen, ketorolac, ketotifen, labetalol, lafutidine, lamifiban, lamivudine, lamotrigine, lanatoside c, lansoprazole, lasofoxifene, leflunomide, leminoprazole, lercanadipine, lesopitron, letrozole, leucovorin, levalbuterol, levallorphan, levetiracetam, levobunolol, levodopa, levofloxacin, levonorgestrel, levophacetoperane, levorphanol, lidoflazine, lifibrol, limaprost, linezolid, lintitript, liranaftate, lisinopril, lisuride, lobeline, lobucavir, lodoxamide, lomefloxacin, lomerizine, lomustine, loperamide, lopinavir, loprazolam, loracarbef, loratadine, lorazepam, lorefloxacin, lormetazepam, losartan, lovastatin, loxapine succinate, loxapine, 1-threo-methylphenidate, lumiracoxib, lynestrenol, lysine acetylsalicylate, lysozyme, lysuride, mabuterol, mafenide, magnesium acetylsalicylate, malgramostin, mannitol hexanitrate, maprotiline, mazindol, mebendazole, meclizine, meclofenamic acid, mecloxaminepentapiperide, medazepam, medibazine, medigoxin, medrogestone, medroxyprogesterone acetate, mefenamic acid, mefenorex, mefloquine, megestrol acetate, megestrol, melengestrol acetate, melphalan, mematine, mepenzolate bromide, meperidine, mephenoxalone, mephentermine, mepindolol, mepixanox, meprobamate, meptazinol, mercaptopurine, merropenum, mesalamine, mesalazine, mesoridazine, besylate, mesoridazine, mestranol, metaclazepam, metamfepramone, metampicillin, metaproterenol, metaraminol, methacycline, methadone hydrochloride, methadone, methamphetamine, methaqualone, methoin, methotrexate, methoxamine, methsuximide, methylhexaneamine, methylphenidate, d-threo-methylphenidate, methylphenobarbitone, methylprednisolone, methysergide, metiazinic acid, metizoline, metoclopramide, metolazone, metoprolol, metoxalone, metripranolol, metronidazole, mexiletine, mexilitene, mianserin, mibefradil, midazolam, midodrine, miglitol, milnacipran, milrinone, minoxidil, mirtazapine, misoprostol, mitomycin, mitotane, mitoxantrone, mizolastine, modafinil, mofebutazone, mofetil, molindone hydrochloride, molindone, molsidomine, monatepil, montelukast, monteplase, moprolol, moricizine, morphine hydrochloride, morphine sulfate, morphine, morpholine salicylate, mosapramine, moxifloxacin, moxisylyte, moxonidine, mycophenolate, nabumetone, nadolol, nadoxolol, nadroparin, nafamostat, nafronyl, naftopidil, nalbuphine, nalidixic acid, nalmefene, nalorphine, naloxone, naltrexone, nandrolone benzoate, nandrolone cyclohexanecarboxylate, nandrolone cyclohexane-propionate, nandrolone decanoate, nandrolone furylpropionate, nandrolone phenpropionate, naphazoline, naproxen, naratriptan, natamycin, nateglinide, nebivalol, nedocromil, nefazodone, nefopam, nelfinavir, nemonapride, neomycin undecylenate, neomycin, neotrofin, nesiritide, n-ethylamphetamine, nevibulol, nevirapine, nexopamil, nicametate, nicardipine, nicergoline, nicofibrate, nicofuranose, nicomorphine, nicorandil, nicotinyl alcohol, nicoumalone, nifedipine, nifenalol, nikethamide, nilutamide, nilvadipine, nimodipine, nimorazole, nipradilol, nisoldipine, nitisinone, nitrazepam, nitrofurantoin, nitrofurazone, nitroglycerin, nizatidine, norastemizole, norepinephrine, norethindrone acetate, norethindrone, norethisterone acetate, norethisterone, norethynodrel, norfenefrine, norfloxacin, norgestimate, norgestrel, norgestrienone, normethadone, normethisterone, normorphine, norpseudoephedrine, nortriptyline, novantrone, nylidrin, octamylamine, octodrine, octopamine, ofloxacin, olanzapine, olapatadine, olmesartan, olopatidine, olsalazine, omapatrilat, omeprazole, ondasetron, opium, oprevelkin, orlistat, ornidazole, ornoprostil, oseltamivir, oxaliplatin, oxamniquine, oxandrolone, oxantel embonate, oxaprozin, oxatomide, pemirolast, oxazepam, oxcarbazepine, oxfendazole, oxiconazole, oxiracetam, oxolinic acid, oxprenolol, oxycodone, oxyfedrine, oxymetazoline, oxymorphone, oxyphenbutazone, oxyphencyclimine, oxyprenolol, ozagrel, paclitaxel, palonosetron, pantoprazole, papaverine, paracalcitol, paramethadione, parecoxib, paripirazole, paromomycin, paroxetine, parsalmide, pazinaclone, pemoline, penbutolol, penciclovir, penicillin G benzathine, penicillin G procaine, penicillin V, penicillins, pentaerythritol tetranitrate, pentapiperide, pentazocine, pentifylline, pentigetide, pentobarbitone, pentorex, pentoxifylline, pentrinitrol, perenzepine, pergolide, perhexiline, perindopril erbumine, perospirone, perphenazine, pimozide, perphenazine, phanquinone, phenacemide, phenacetin, phenazopyridine, phencarbamide, phendimetrazine, phenelzine, phenindione, phenmetrazine, phenobarbitone, phenoperidine, phenothiazines, phenoxybenzamine, phensuximide, phentermine, phentolamine, phenyl salicylate, phenylacetate, phenylbutazone, phenylephrine hydrochloride, phenylpropanolamine hydrochloride, phenylpropanolamine hydrochloride, phenylpropyl-methylamine, phenytoin, phloroglucinol, pholedrine, physostigmine salicylate, physostigmine, phytonadiol, piapenum, picilorex, piclamilast, picrotoxin, picumast, pifamine, pilsicainide, pimagedine, pimeclone, pimecrolimus, pimethylline, pimozide, pinaverium bromide, pindolol, pioglitazone, piperacillin, piperazine estrone sulfate, piperazine derivatives, piperilate, piracetam, pirbuterol, pirenzepine, piribedil, pirifibrate, piroxicam, pitavastatin, pizotyline, plaunotol, polaprezinc, polybenzarsol, polyestrol phosphate, practolol, pralnacasan, pramipexole, pranlukast, prasterone, pravastatin, prazepam, praziquantel, prazosin, prednisolone, prednisone, pregabalin, prenalterol, prenylamine, pridinol, prifinium bromide, primidone, primipramine, probenecid, probucol, procainamide, procarbazine, procaterol, prochlorperazine, progesterone, proguanil, pronethalol, propafenone, propamidine, propatyl nitrate, propentofyline, propiram, propoxyphene, propranolol, propylhexedrine, propylthiouracil, protokylol, protriptyline, proxazole, pseudoephedrine, purines, pyrantel embonate, pyrazoles, pyrazolones, pyridofylline, pyrimethamine, pyrimidines, pyrrolidones, quazepam, quetiapine, quetuapine, quinagolide, quinapril, quinestrol, quinfamide, quinidine, quinine sulfate, quinolones, quinupritin, rabalzotan, rabeprazole sodium, rabeprazole, racefimine, ramatroban, ramipril, ranitidine, ranolazine, ransoprazole, rasagiline, rebamipide, refludan, repaglinide, repinotan, repirinast, reproterol, reserpine, retinoids, ribavirin, rifabutine, rifampicin, rifapentine, rilmenidine, riluzole, rimantadine, rimiterol, rioprostil, risperidone, ritanovir, ritapentine, ritipenem, ritodrine, ritonavir, rivastigmine, rizatriptan, rociverine, rofecoxib, rohypnol, rolipram, romoxipride, ronifibrate, ropinirole, ropivacaine, rosaprostol, rosiglitazone, rosuvastatin, rotinolol, rotraxate, roxatidine acetate, roxindole, rubitecan, salacetamide, salicin, salicylamide, salicylic acid derivatives, salmeterol, saquinavir, scopolamine, secnidazole, selegiline, semotiadil, seratrodast, sertindole, sertraline, sibutramine, sildenafil, simfibrate, simvastatin, siramesine, sirolimus, sitaxsentan, sofalcone, somotiadil, sorivudine, sotalol, soterenol, sparfloxacin, spasmolytol, spectinomycin, spiramycin, spironolactone, spizofurone, stanozolol, stavudine, streptomycin, succinylsulfathiazole, sucralfate, sufentanil, sulconazole nitrate, sulfacetamide, sulfadiazine, sulfaloxic acid, sulfarside, sulfinalol, sulindac, suloctidil, sulphabenzamide, sulphacetamide, sulphadiazine, sulphadoxine, sulphafurazole, sulphamerazine, sulphamethoxazole, sulphapyridine, sulphasalazine, sulphinpyrazone, sulpiride, sulthiame, sultopride, sultroponium, sumanirole, sumatriptan, sunepitron, superoxide dismutase, suplatast, suramin sodium, synephrine, tacrine, tacrolimus, tadalafil, talinolol, talipexole, tamoxifen, tamsulosin, targretin, tazanolast, tazarotene, tazobactum, tecastimezole, teclozan, tedisamil, tegaserod, telenzepine, telmisartan, temazepam, teniposide, teprenone, terazosin, terbutaline sulfate, terbutaline, terfenadine, terodiline, terofenamate, tertatolol, testolactone, testosterone, tetracyclics, tetracycline, tetrahydrocannabinol, tetrahydrozoline, thalidomide, theofibrate, thiabendazole, thiazinecarboxamides, thiocarbamates, thiocarbamizine, thiocarbarsone, thioridazine, thiothixene, tiagabine, tiamenidine, tianeptine, tiaprofenic acid, tiaramide, ticlopidine, tigloidine, tilisolol, timolol, tinidazole, tinofedrine, tinzaparin, tipranavir, tirapazamine, tirofiban, tiropramide, titanicene, tizanidine, tocainide, tolazamide, tolazoline, tolbutamide, tolcapone, tolciclate, tolfenamic acid, toliprolol, tolterodine, tonaberstat, topiramate, topotecan, torasemide, toremifene citrate, toremifene, tosufloxacin, tramadol, tramazoline, trandolapril, tranilast, tranylcypromine, trapidil, traxanox, trazodone, tretoquinol, triamcinolonc, triamterine, triazolam, triazoles, tricromyl, tricyclics, trifluoperazine hydrochloride, trifluoperazine, triflupromazine, trifluridine, trihexyphenidyl hydrochloride, trihexyphenidyl, trimazosin, trimebutine, trimetazidine, trimethoprim, trimgestone, trimipramine, trimoprostil, trithiozine, troglitazone, trolnitrate phosphate, tromethamine, tropicamide, trovafloxacin, troxipide, tuaminoheptane, tulobuterol, tymazoline, tyramine, undecanoate, undecanoic acid, urinastatin, ursodeoxycholic acid, valacyclovir, valdecoxib, valerate, valganciclovir, valproic acid, valsartan, vancomycin, vardenafil, venlafaxine, vinorelbine, verapamil, vidarabine, vigabatrin, vincamine, vinpocetine, viomycin, viquidil, visnadine, vitamin a derivatives, vitamin a, vitamin b2, vitamin d, vitamin e, vitamin k, voglibose, voriconazole, xaliproden, xamoterol, xanthinol niacinate, xenytropium bromide, xibenolol, ximelagatran, xylometazoline, yohimbine, zacopride, zalirlukast, zafirlukat, zalcitabine, zaleplon, zanamivir, zatebradine, ziconotide, zidovudine, zileuton, zimeldine, zinc propionate, ziprasidone, zolimidine, zolmitriptan, zolpidem, zonisamide, zopiclone, lidocaine, articaine, bupivacaine, chloroprocaine, etidocaine, levobupivacaine, oxyprocaine, mepivacaine, piperocaine, prilocaine, tetracaine, procaine, dibucaine, benzocaine, dyclaine, amorolfine, isoconazole, clotrimazole, econazole, econazole nitrate, miconazole, nystatin, terbinafine, bifonazole, amphotericin, griseofulvin, ketoconazole, fluconazole and flucytosine, salicylic acid, fezatione, ticlatone, tolnaftate, triacetin, pyrithione, zinc pyrithione, sodium pyrithione, butenafine, butoconazole, butoconazole nitrate, clioquinol, itraconazole, lanoconazole, neticonazole, tioconazole, terconazole, ciclopirox olamine, octanoic acid, sorbic acid, hexanoic acid, triclosan, or benzoic acid.

For example, the therapeutic compound may be selected from one or more of the following:

an agent for the alimentary system including antidiarrhoeals such as diphenoxylate, loperamide and hyoscyamine;

an agent for the cardiovascular system including antihypertensives such as hydralazine, minoxidil, captopril, enalapril, clonidine, prazosin, debrisoquine, diazoxide, guanethidine, methyldopa, reserpine, and trimetaphan, calcium channel blockers such as diltiazem, felodopine, amlodipine, nitrendipine, nifedipine and verapamil, antiarrhyrthmics such as amiodarone, flecainide, disopyramide, procainamide, mexiletene and quinidine, antiangina agents such as glyceryl trinitrate, erythritol tetranitrate, pentaerythritol tetranitrate, mannitol hexanitrate, perhexilene, isosorbide dinitrate and nicorandil, beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate, cardiotonic glycosides such as digoxin and other cardiac glycosides and theophylline derivatives, adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine, vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol, and antimigraine preparations such as ergotamine, dihydroergotamine, methysergide, pizotifen and sumatriptan;

drugs affecting blood and haemopoietic tissues including anticoagulants and thrombolytic agents such as warfarin, dicoumarol, low molecular weight heparins such as enoxaparin, streptokinase and its active derivatives, and haemostatic agents such as aprotinin, tranexamic acid and protamine;

an agent for central nervous system including analgesics, antipyretics including the opiod analgesics such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine and dihydrocodeine, and others include acetylsalicylic acid (aspirin), paracetamol, and phenazone, hypnotics and sedatives such as the barbiturates, amylobarbitone, butobarbitone and pentobarbitone and other hypnotics and sedatives such as choral hydrate, chlormethiazole, hydroxyzine and meprobamate, antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam, neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium, antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline, CNS stimulants such as caffeine, anti-alzheimer's agents such as tacrine, antiparkinson agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923), anticonvulsants such as phenytoin, valproic acid, primidone, phenobarbitone, methylphenobarbitone and carbamazepine, ethosuximide, methsuximide, phensuximide, sulthiame and clonazepam, antiemetics, antinauseants such as the phenothiazines, prochloperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride;

an agent for musculoskeletal system including non-steroidal anti-inflammatory agents including their racemic mixtures or individual enantiomers where applicable, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketoralac, and additional non-steroidal antiinflammatory agents which can be formulated in combination with the dermal penetration enhancers include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate, antirheumatoid agents such as penicillamine, aurothioglucose, sodium aurothiomalate, methotrexate and auranofin, muscle relaxants such as baclofen, diazepam, cyclobenzaprine hydrochloride, dantrolene, methocarbamol, orphenadrine and quinine, agents used in gout and hyperuricaemia such as allopurinol, colchicine, probenecid and sulphinpyrazone;

hormones and steroids including oestrogens such as oestradiol, oestriol, oestrone, ethinyloestradiol, mestranol, stilboestrol, dienoestrol, epioestriol, estropipate and zeranol, progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol, antiandrogens such as cyproterone acetate and danazol, antioestrogens such as tamoxifen and epitiostanol and the aromatase inhibitors, exemestane and 4-hydroxy-androstenedione and its derivatives, androgens and anabolic agents such as testosterone, methyltestosterone, clostebol acetate, drostanolone, furazabol, nandrolone oxandrolone, stanozolol, trenbolone acetate, dihydro-testosterone, 17-.alpha.-methyl-19-nortestosterone and fluoxymesterone, 5-alpha reductase inhibitors such as finasteride, turosteride, LY-191704 and MK-306, corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide, and further examples of steroidal antiinflammatory agents including cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, ilucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol, pituitary hormones and their active derivatives or analogs such as corticotrophin, thyrotropin, follicle stimulating hormone (FSH), luteinising hormone (LH) and gonadotrophin releasing hormone (GnRH), hypoglycaemic agents such as insulin, chlorpropamide, glibenclamide, gliclazide, glipizide, tolazamide, tolbutamide and metformin, thyroid hormones such as calcitonin, thyroxine and liothyronine and antithyroid agents such as carbimazole and propylthiouracil, and other miscellaneous hormone agents such as octreotide, pituitary inhibitors such as bromocriptine, and ovulation inducers such as clomiphene;

an agent for the genitourinary system including diuretics such as the thiazides, related diuretics and loop diuretics, bendrofluazide, chlorothiazide, chlorthalidone, dopamine, cyclopenthiazide, hydrochlorothiazide, indapamide, mefruside, methychlothiazide, metolazone, quinethazone, bumetanide, ethacrynic acid and frusemide and potassium-sparing diuretics, spironolactone, amiloride and triamterene, antidiuretics such as desmopressin, lypressin and vasopressin including their active derivatives or analogs, obstetric drugs including agents acting on the uterus such as ergometrine, oxytocin and gemeprost, and prostaglandins such as alprostadil (PGE1), prostacyclin (PGI2), dinoprost (prostaglandin F2-alpha) and misoprostol;

antimicrobials such as antimicrobials including the cephalosporins such as cephalexin, cefoxytin and cephalothin, penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin, tetracyclines such as minocycline, chlortetracycline, tetracycline, demeclocycline, doxycycline, methacycline and oxytetracycline and other tetracycline-type antibiotics, aminoglycosides such as amikacin, gentamicin, kanamycin, neomycin, netilmicin and tobramycin, antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc pyrithione and sodium pyrithione, triclosan, quinolones such as nalidixic acid, cinoxacin, ciprofloxacin, enoxacin and norfloxacin, sulphonamides such as phthalylsulphthiazole, sulfadoxine, sulphadiazine, sulphamethizole and sulphamethoxazole, sulphones such as dapsone, other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoyl peroxide, antituberculosis drugs such as ethambutol, isoniazid, pyrazinamide, rifampicin and clofazimine, antimalarials such as primaquine, pyrimethamine, chloroquine, hydroxychloroquine, quinine, mefloquine and halofantrine, antiviral agents such as acyclovir and acyclovir prodrugs, famciclovir, zidovudine, didanosine, stavudine, lamivudine, zalcitabine, saquinavir, indinavir, ritonavir, n-docosanol, tromantadine and idoxuridine, anthelmintics such as mebendazole, thiabendazole, niclosamide, praziquantel, pyrantel embonate and diethylcarbamazine, and cytotoxic agents such as plicamycin, cyclophosphamide, dacarbazine, fluorouracil and its prodrugs, methotrexate, procarbazine, 6-mercaptopurine and mucophenolic acid;

an agent for metabolism including anorectic and weight reducing agents such as dexfenfluramine, fenfluramine, diethylpropion, mazindol and phentermine, agents used in hypercalcaemia such as calcitriol, dihydrotachysterol and their active derivatives or analogs;

an agent for the respiratory system such as antitussives such as ethylmorphine, dextromethorphan and pholcodine, expectorants such as acetylcysteine, bromhexine, emetine, guaiphenesin, ipecacuanha and saponins, decongestants such as phenylephrine, phenylpropanolamine ans pseudoephedrine, bronchospasm relaxants such as ephedrine, fenoterol, orciprenaline, rimiterol, salbutamol, sodium cromoglycate, cromoglycic acid and its prodrugs, terbutaline, ipratropium bromide, salmeterol and theophylline and theophylline derivatives;

an agent for allergy and the immune system such as antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

local anaesthetics such as bupivacaine, amethocaine, lignocaine, cinchocaine, dibucaine, mepivacaine, prilocaine and etidocaine;

stratum corneum lipids, such as ceramides, cholesterol and free fatty acids, for improved skin barrier repair;

neuromuscular blocking agents such as suxamethonium, alcuronium, pancuronium, atracurium, gallamine, tubocurarine and vecuronium;

smoking cessation agents such as nicotine, bupropion and ibogaine;

insecticides and other pesticides which are suitable for local or systemic application; and dermatological agents, such as vitamins A and E, vitamin E acetate and vitamin E sorbate, allergens for desensitisation such as house dust mite allergen, nutritional agents, such as vitamins, essential amino acids and essential fats, keratolytics such as the alpha-hydroxy acids, glycollic acid and salicylic acid, psychic energisers, such as 3-(2-aminopropyl)indole, 3-(2-aminobutyl)indole, and the like, anti-acne agents such as containing isotretinoin, tretinoin and benzoyl peroxide, antipsoriasis agents such as containing etretinate, cyclosporin and calcipotriol, anti-itch agents such as capsaicin and its derivatives such as nonivamide, and anticholinergic agents which are effective for the inhibition of axillary sweating and for the control of prickly heat, such as the antiperspirant activity of agents such as methatropine nitrate, propantheline bromide, scopolamine, methscopolamine bromide, and the new class of soft antiperspirants, quaternary acyloxymethyl ammonium salts.

In certain embodiments of the present invention, more than one therapeutic agent (e.g., more than one of the therapeutic agents listed above) may be present in the drug delivery system according to the present invention. In certain embodiments of the drug delivery system of the present invention, the therapeutic agent may be a combination of more than one therapeutic agent listed above.

In certain embodiments, the therapeutic compound is not an anesthetic agent, such as a local anesthetic agent. In certain embodiments, the therapeutic compound is not an antifungal agent. In certain embodiments, the therapeutic compound is not lidocaine, articaine, bupivacaine, chloroprocaine, etidocaine, levobupivacaine, oxyprocaine, mepivacaine, piperocaine, prilocaine, tetracaine, procaine, dibucaine, benzocaine, dyclaine, amethocaine, lignocaine, cinchocaine, amorolfine, isoconazole, clotrimazole, econazole, econazole nitrate, miconazole, nystatin, terbinafine, bifonazole, amphotericin, griseofulvin, ketoconazole, fluconazole and flucytosine, salicylic acid, fezatione, ticlatone, tolnaftate, triacetin, pyrithione, zinc pyrithione, sodium pyrithione, butenafine, butoconazole, butoconazole nitrate, clioquinol, itraconazole, lanoconazole, neticonazole, tioconazole, terconazole, ciclopirox olamine, octanoic acid, sorbic acid, hexanoic acid, triclosan, or benzoic acid.

In certain embodiments wherein a specific therapeutic agent is duplicated in the exemplary listings above, no preferential indication is intended. Rather, certain agents above are repeated for the purpose of providing clarity as to the classes of agents suitable for the topical formulation system of the present invention as well as the individual agents suitable for the topical formulation system of the present invention.

The term "volatile component" as used herein refers to a component (e.g., a solvent or combination of solvents) that changes readily from solid or liquid to a vapor, e.g., that evaporates readily at some temperature at or below body temperature and less readily at room temperature, such as a component that evaporates rapidly between 21 and 37° C. at atmospheric pressure.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMOs.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the term "saturation" refers to the point at which a solution of a substance (e.g., a therapeutic agent) can dissolve no more of that substance and additional amounts of it will appear as a precipitate. The phrase "near saturation" refers to a solution which is at least 90% saturated, such as 90%, 91%, 92%, 93%, 94%, 95%, 96%, 97%, 98%, or 99% saturated. The phrase "above saturation" refers to a solution which has a higher concentration of substance (e.g., a therapeutic agent) than the concentration at which the solution is saturated (e.g., it is greater than 100% saturated).

The drug delivery system and methods of the present invention may be utilized to treat an individual in need thereof. In certain embodiments, the individual is a mammal such as a human, or a non-human mammal The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The drug delivery system of the present invention can be administered to a subject topically, for example, as a gel, foam, solution, lotion, cream, ointment or spray applied to the skin. Details of appropriate routes of administration and compositions suitable for same can be found in, for example, U.S. Pat. Nos. 6,110,973, 5,763,493, 5,731,000, 5,541,231, 5,427, 798, 5,358,970 and 4,172,896, as well as in patents cited therein.

The drug delivery system may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the therapeutic agent which produces a therapeutic effect.

Besides the components outlined above, the drug delivery system of the present invention can also include adjuvants such as wetting agents, emulsifying and suspending agents, sweetening, flavoring, coloring, perfuming and preservative agents.

Drug delivery systems of the present invention for topical or transdermal administration include powders, sprays, ointments, pastes, creams, lotions, gels, solutions, patches and inhalants. The therapeutic agent may be mixed under sterile conditions with the other components of the drug delivery system, and with any preservatives, buffers, or propellants that may be required.

The ointments, pastes, creams and gels may contain, in addition to the therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Sprays can contain, in addition to a therapeutic agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The drug delivery systems of the present invention may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like.

Actual dosage levels of the active ingredients in the drug delivery system may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular therapeutic agent or combination of therapeutic agents employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the drug delivery system required. For example, the physician or veterinarian could start doses of the drug delivery system or therapeutic agent at levels lower than that required in order to achieve the desired therapeutic effect and gradually increase the dosage until the desired effect is achieved. By "therapeutically effective amount" is meant the concentration of a therapeutic agent that is sufficient to elicit the desired therapeutic effect. It is generally understood that the effective amount of the therapeutic agent will vary according to the weight, sex, age, and medical history of the subject. Other factors which influence the effective amount may include, but are not limited to, the severity of the patient's condition, the disorder being treated, the stability of the therapeutic agent, and, if desired, another type of therapeutic agent being administered with the therapeutic agent of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active therapeutic agent used in the drug delivery systems and methods of the invention will be that amount of the therapeutic agent that is the lowest dose effective to produce a therapeutic effect. Such an effective dose will generally depend upon the factors described above.

If desired, the effective daily dose of the active therapeutic agent may be administered as one, two, three, four, five, six or more sub-doses administered separately at appropriate intervals throughout the day, optionally, in unit dosage forms. In certain embodiments of the present invention, the active therapeutic agent may be administered two or three times daily. In further embodiments, the active therapeutic agent will be administered once daily.

The patient receiving this treatment is any animal in need, including primates, in particular humans, and other mammals such as equines, cattle, swine and sheep; and poultry and pets in general.

In certain embodiments, the drug delivery system of the present invention may optionally be administered conjointly with another therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same drug delivery system or in a separate formulation, either concomitantly or sequentially. Thus, an individual who receives such treatment can benefit from a combined effect of different therapeutic compounds.

This invention includes the use of pharmaceutically acceptable salts of the therapeutic compounds listed above. In certain embodiments, contemplated salts of the invention include alkyl, dialkyl, trialkyl or tetra-alkyl ammonium salts. In certain embodiments, contemplated salts of the invention include Na, Ca, K, Mg, Zn or other metal salts.

Wetting agents, emulsifiers and lubricants, such as sodium lauryl sulfate, as well as coloring agents, release agents, and perfuming agents, preservatives and antioxidants can also be present in the drug delivery systems.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The present invention provides a kit comprising:
a) a drug delivery system for topical administration of a therapeutic agent comprising
  i) a first component which is a therapeutic agent, such as any one of the therapeutic agents listed above, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature, or any $C_{12}$ to $C_{22}$ mono- or poly-unsaturated or branched chain alcohol or corresponding acid which is a liquid at room temperature, and iv) a fourth component which is a volatile component, such as one or more short-chain alcohols, volatile silicones, or combinations thereof; and
b) instructions for the administration of the drug delivery system to an individual in need thereof.

In certain embodiments, the kit further comprises instructions for the administration of the drug delivery system conjointly with another therapeutic agent. In certain embodiments, the kit further comprises a second pharmaceutical formulation, including but not limited to a drug delivery system according to the present invention comprising a second therapeutic agent.

In certain embodiments, the invention relates to a method for conducting a pharmaceutical business, by manufacturing a drug delivery system of the present invention, or a kit as described herein, and marketing to healthcare providers the benefits of using the drug delivery system or kit for the treatment of an individual in need thereof.

In certain embodiments, the invention relates to a method for conducting a pharmaceutical business, by providing a distribution network for selling a drug delivery system of the present invention, or kit as described herein, and providing instruction material to patients or physicians for using the drug delivery system or kit for the treatment of an individual in need thereof.

In certain embodiments, the invention comprises a method for conducting a pharmaceutical business, by determining an appropriate drug delivery system of the present invention comprising an appropriate dosage of a therapeutic agent for the treatment of an individual in need thereof, conducting therapeutic profiling of identified drug delivery systems for efficacy and toxicity in animals, and providing a distribution network for selling an identified drug delivery system as having an acceptable therapeutic profile. In certain embodiments, the method further includes providing a sales group for marketing the drug delivery system to healthcare providers.

In certain embodiments, the invention relates to a method for conducting a pharmaceutical business by determining an appropriate drug delivery system of the present invention comprising an appropriate dosage of a therapeutic agent for the treatment of an individual in need thereof, and licensing, to a third party, the rights for further development and sale of the formulation.

EXEMPLIFICATION

Example 1

Two formulations were evaluated comprising the following components:

4% lidocaine
4% propylene glycol
4% oleyl alcohol
2 or 3% hydroxypropylcellulose
68 or 69% isopropyl alcohol (IPA)
17% hexamethyldisiloxane.

Formulation #1 contained 3% hydroxypropylcellulose (e.g., KLUCEL™ (hydroxypropylcellulose)) and 68% isopropyl alcohol. Formulation #2 contained 2% hydroxypropylcellulose (e.g., KLUCEL™ (hydroxypropylcellulose)) and 69% isopropyl alcohol. Both formulations were clear to translucent liquids. Formulation #1 was slightly thicker than Formulation #2 but both were sufficiently viscous so as not to drip when applied. Product was placed around the area of the lips with a cotton swab and then rubbed into the area.

Patient #1—Formulation #1—experienced numbness almost immediately and was able to be injected after 15 minutes exposure. No pain due to the needle stick was noted.

Patient #2—Formulation #2—experienced numbness almost immediately and was able to be injected after 15 minutes exposure. Patient indicated that the pain at injection was similar to previous procedures that utilized lidocaine/prilocaine cream sold under the brand name EMLA. However, previous procedures allowed the EMLA to remain on the skin for over 60 minutes prior to injection.

Patient #3—Formulation #1—two applications 15 minutes apart were made. Patient experienced pain on injections similar to previous injections. Again, previous procedures utilized EMLA with greater than 60 minutes exposure.

Patient #4—Formulations #1 and #2—Products were applied to the left and right side of the site to evaluate the products side-by-side. Formulation #1 was judged superior by the patient; numbness was experienced more quickly. Injections were made 15 to 20 minutes after application.

Two additional patients were evaluated. Samples were applied as per Patient #4 above. In both cases, Formulation #1 was judged superior. In addition, one patient that required removal of a growth was treated with Formulation #1 and, after 15 minutes, had no pain at the site of biopsy.

Example 2

The application of a drug delivery system according to the present invention was tested prior to the injection of 4 units of Botox® (onabotulinumtoxinA) to the crow's feet wrinkles.

A topical anesthetic comprising 4% lidocaine, 4% propylene glycol, 4% oleyl alcohol, 1.75% hydroxypropylcellulose, 69.25% isopropyl alcohol (IPA), and 17% hexamethyldisiloxane was prepared for use in the following dermatological procedures.

Twelve subjects received a total of six Botox® (onabotulinumtoxinA) injections at four units each in six separate zones demarcated in the lateral periocular regions bilaterally. The six zones are depicted in FIG. 1. The administration of the injections to the specific zones was randomized among the subjects. The first injection was administered at time 0 minutes in the absence of the topical anesthetic solution. Following the initial injection, the topical anesthetic solution described above was applied to the remaining 5 zones. Injections were then given at 5 minutes, 15 minutes, 25 minutes, 35 minutes, and 45 minutes following application of the anesthetic solution. Immediately following each injection, patients were asked to rank their perceived pain on the visual analog scale (VAS) from 1-10. Patients were instructed that 1 indicates "no pain", 5 indicates "moderate pain", and 10 indicates "worst pain". A ranking of 3 is generally believed to indicate minimal pain, and a ranking of two or less is generally believed to indicate almost no perceived pain.

The average pain perceived on the VAS at times 0 minutes, 5 minutes, 15 minutes, 25 minutes, 35 minutes, and 45 minutes was 5.2±2.4, 5.8±2.7, 5.0±2.6, 3.1±1.8, 1.9±1.7, and 2.7±2.2, respectively. The data shows a slight increase in perceived pain from time 0 minutes to time 5 minutes with the least amount of pain experienced at time 35 minutes.

Three subjects experienced mild burning and irritation to the skin as well as slight irritation of the eyes following application of the topical anesthetic solution to the lateral periocular regstions. However, no redness or irritation was observed.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A drug delivery system for topical administration of a therapeutic agent comprising the therapeutic agent lidocaine present in an amount of 4% by weight, propylene glycol in an amount between 2 and 6% by weight, oleyl alcohol in an amount between 2 and 6% by weight, and a volatile component comprising a volatile polydimethylsiloxane in an amount between 60 and 90% by weight.

2. The drug delivery system of claim 1, further comprising a thickener.

3. The drug delivery system of claim 2, wherein the drug delivery system comprises between 0.1 and 3.5 percent by weight of the thickener.

4. The drug delivery system of claim 2 or 3, wherein the thickener comprises hydroxypropylcellulose.

5. A method for administering the drug delivery system of claim 1 to an animal in need of such treatment, comprising applying an effective amount of the drug delivery system.

6. A method for the treatment or prophylaxis of a disease or condition in an animal comprising administering to a dermal surface of an animal in need of such treatment a therapeutically effective amount of a drug delivery system according to claim 1.

7. The method of claim 5 or 6, wherein the animal is a human.

8. The drug delivery system of claim 1, wherein the propylene glycol and oleyl alcohol are present in a ratio of 1:1.

9. The drug delivery system of claim 1, wherein the volatile component comprising a volatile polydimethylsiloxane is a linear or cyclic polydimethylsiloxane compound having a viscosity from about 0.5 to about 10 cst.

10. The drug delivery system of claim 9, wherein the linear polydimethylsiloxane is selected from the group consisting of hexamethyldisiloxane, decamethyltetrasiloxane, octamethyltrisiloxane, decamethylpentasiloxane and combinations thereof.

11. The drug delivery system of claim 10, wherein the linear polydimethylsiloxane is hexamethyldisiloxane.

12. The drug delivery system of claim 11, wherein the hexamethyldisiloxane has a viscosity of 0.65 cST.

13. The drug delivery system of claim 9, wherein the cyclic polydimethylsiloxane compound is a cyclomethicone.

14. The drug delivery system of claim 1, wherein the volatile component further comprises one or more short-chain alcohols.

15. The drug delivery system of claim 1, wherein the volatile component is present in an amount of between 60 and 85 percent by weight.

* * * * *